(12) United States Patent
Stark

(10) Patent No.: US 11,045,231 B2
(45) Date of Patent: *Jun. 29, 2021

(54) METHODS FOR DELIVERY OF SCREWS FOR JOINT FUSION

(71) Applicant: Ilion Medical, Inc., Minneapolis, MN (US)

(72) Inventor: John G. Stark, Deephaven, MN (US)

(73) Assignee: Ilion Medical, Inc., Minneapolis, MN (US)

( * ) Notice: Subject to any disclaimer, the term of this patent is extended or adjusted under 35 U.S.C. 154(b) by 724 days.

This patent is subject to a terminal disclaimer.

(21) Appl. No.: 15/586,414

(22) Filed: May 4, 2017

(65) Prior Publication Data
US 2017/0238973 A1    Aug. 24, 2017

Related U.S. Application Data

(63) Continuation of application No. 14/149,197, filed on Jan. 7, 2014, now Pat. No. 9,668,781, which is a
(Continued)

(51) Int. Cl.
*A61B 17/70* (2006.01)
*A61B 17/86* (2006.01)

(52) U.S. Cl.
CPC ...... *A61B 17/7055* (2013.01); *A61B 17/8625* (2013.01)

(58) Field of Classification Search
CPC .... A61F 2/4603; A61F 2/4607; A61F 2/4611; A61B 17/86; A61B 17/8625;
(Continued)

(56) References Cited

U.S. PATENT DOCUMENTS

| 4,569,338 A | 2/1986 | Edwards |
| 4,640,271 A | 2/1987 | Lower |

(Continued)

FOREIGN PATENT DOCUMENTS

| JP | 08024281 | 1/1996 |
| WO | 95-35180 | 12/1995 |

OTHER PUBLICATIONS

Presentation by Dr. John G. Stark, Minnesota Orthopedic Society, Eighteenth Annual Meeting, May 2002.
(Continued)

*Primary Examiner* — Si Ming Ku
(74) *Attorney, Agent, or Firm* — Christensen, Fonder, Dardi & Herbert PLLC; Peter S. Dardi

(57) ABSTRACT

Procedures for the fusion of the sacroiliac joint advantageously make use of an implant selected to distract the joint upon insertion and to maintain or increase tension upon insertion. The implant can have a varying structure along its length. In some method described herein for fusing the sacroiliac joint using an implant, an implant is screwed into the sacroiliac joint between the sacrum bone and the iliac bone. The implant comprises a shaft, a tool engagement flange at top end of the shaft, a pointed tip comprising no more than about 20 percent of the length of the screw, and threads spiraling around the shaft. For screws of particular interest, the volume displacement perpendicular to the shaft increases at least about 5 percent from a point adjacent the tip to a point near the top of the shaft. Some of the desirable screw designs can be used in other orthopedic application, especially situations involving varying bone hardness. Useful filler material can be formed from a blend of bone powder and bioactive agents.

19 Claims, 7 Drawing Sheets

Related U.S. Application Data continuation of application No. 12/651,843, filed on Jan. 4, 2010, now abandoned, which is a continuation of application No. 11/879,536, filed on Jul. 17, 2007, now abandoned.

(58) Field of Classification Search
CPC . A61B 17/863; A61B 17/8635; A61B 17/864; A61B 17/8645; A61B 17/7055
See application file for complete search history.

(56) References Cited

U.S. PATENT DOCUMENTS

| | | |
|---|---|---|
| 4,772,287 A | 9/1988 | Ray et al. |
| 4,950,270 A | 8/1990 | Bowman et al. |
| 4,961,740 A | 10/1990 | Ray et al. |
| 5,015,247 A | 5/1991 | Michelson |
| 5,015,255 A * | 5/1991 | Kuslich ............... A61B 17/1671 128/898 |
| 5,226,766 A | 7/1993 | Lasner |
| 5,242,444 A | 9/1993 | MacMillan |
| 5,294,227 A | 3/1994 | Forster et al. |
| 5,334,209 A | 8/1994 | Cain |
| 5,336,225 A | 8/1994 | Zang |
| 5,368,593 A | 11/1994 | Stark |
| 5,443,509 A | 8/1995 | Boucher et al. |
| 5,456,267 A | 10/1995 | Stark |
| 5,470,334 A | 11/1995 | Ross et al. |
| 5,492,442 A | 2/1996 | Lasner |
| 5,607,432 A | 3/1997 | Fucci |
| 5,669,909 A * | 9/1997 | Zdeblick ............... A61F 2/4611 606/247 |
| 5,741,253 A | 4/1998 | Michelson |
| 5,741,261 A | 4/1998 | Moskovitz et al. |
| 5,743,914 A | 4/1998 | Skiba |
| 5,772,594 A | 6/1998 | Barrick |
| 5,865,847 A | 2/1999 | Kohrs et al. |
| 5,871,486 A | 2/1999 | Huebner et al. |
| 5,906,616 A * | 5/1999 | Pavlov ................. A61F 2/4611 606/247 |
| 5,919,193 A | 7/1999 | Slavitt |
| 5,928,239 A | 7/1999 | Mirza |
| 5,964,768 A | 10/1999 | Huebner |
| 5,993,463 A | 11/1999 | Truwit |
| 6,030,162 A | 2/2000 | Huebner |
| 6,053,916 A | 4/2000 | Moore |
| 6,162,053 A | 12/2000 | Hollander |
| 6,175,758 B1 | 1/2001 | Kambin |
| 6,180,606 B1 | 1/2001 | Chen et al. |
| 6,187,008 B1 | 2/2001 | Hamman |
| 6,283,966 B1 | 9/2001 | Houfburg |
| 6,290,724 B1 | 9/2001 | Marino |
| 6,294,187 B1 | 9/2001 | Boyce et al. |
| 6,306,170 B2 | 10/2001 | Ray |
| 6,351,573 B1 | 2/2002 | Schnieder |
| 6,375,657 B1 | 4/2002 | Doubler et al. |
| 6,479,633 B1 | 11/2002 | Ni et al. |
| 6,511,499 B2 | 1/2003 | Schmieding et al. |
| 6,517,542 B1 | 2/2003 | Papay et al. |
| 6,562,049 B1 | 5/2003 | Norlander et al. |
| 6,589,245 B1 | 7/2003 | Weiler et al. |
| 6,595,995 B2 | 7/2003 | Zdeblick et al. |
| 6,607,487 B2 | 8/2003 | Chang et al. |
| 6,635,059 B2 | 10/2003 | Randall et al. |
| 6,666,888 B1 | 12/2003 | Jackson |
| 6,746,451 B2 | 6/2004 | Middleton et al. |
| 6,807,885 B2 | 10/2004 | Loper |
| 6,863,671 B1 | 3/2005 | Strobel et al. |
| 6,875,215 B2 | 4/2005 | Taras et al. |
| 6,984,235 B2 | 1/2006 | Huebner |
| 7,001,393 B2 | 2/2006 | Schwenke et al. |
| 7,083,647 B1 | 8/2006 | Sklar et al. |
| 2002/0038123 A1 | 3/2002 | Visotsky et al. |
| 2002/0087161 A1 | 7/2002 | Randall et al. |
| 2002/0099288 A1 | 7/2002 | Chang et al. |
| 2002/0183846 A1 | 12/2002 | Kuslich et al. |
| 2003/0032098 A1 | 2/2003 | Young et al. |
| 2003/0065332 A1 | 4/2003 | TenHuisen et al. |
| 2003/0078668 A1 | 4/2003 | Michelson |
| 2003/0114854 A1 | 6/2003 | Pavlov et al. |
| 2003/0153919 A1 | 8/2003 | Harris |
| 2004/0215198 A1 | 10/2004 | Marnay et al. |
| 2004/0228901 A1 | 11/2004 | Trieu et al. |
| 2004/0267365 A1 | 12/2004 | Fornari |
| 2005/0021041 A1 | 1/2005 | Michelson |
| 2005/0038513 A1 | 2/2005 | Michelson |
| 2005/0222619 A1 | 10/2005 | Dreyfuss et al. |
| 2006/0058793 A1 | 3/2006 | Michelson |
| 2006/0084992 A1 | 4/2006 | Michelson |
| 2006/0085068 A1 * | 4/2006 | Barry .................. A61F 2/4611 623/17.11 |
| 2006/0089646 A1 | 4/2006 | Bonutti |
| 2006/0111782 A1 | 5/2006 | Petersen |
| 2006/0122612 A1 | 6/2006 | Justin et al. |
| 2006/0129238 A1 | 6/2006 | Paltzer |
| 2006/0155286 A1 | 7/2006 | Wang |
| 2006/0200139 A1 | 9/2006 | Michelson |
| 2006/0224240 A1 | 10/2006 | Allard et al. |
| 2006/0235522 A1 | 10/2006 | Foley |
| 2007/0027543 A1 * | 2/2007 | Gimble ............... A61L 27/3608 623/17.11 |
| 2007/0032875 A1 | 2/2007 | Blacklock et al. |
| 2007/0055374 A1 | 3/2007 | Copf et al. |
| 2007/0156145 A1 | 7/2007 | Demakas et al. |
| 2008/0009861 A1 | 1/2008 | Stark |
| 2008/0249627 A1 | 10/2008 | Moehlenbruck et al. |
| 2009/0099610 A1 | 4/2009 | Johnson et al. |
| 2009/0259261 A1 | 10/2009 | Reiley |

OTHER PUBLICATIONS

International Search Report for PCT/US2008/008399, dated Dec. 24, 2008.

Supplementary European Search Report from corresponding European Patent Application No. 08780048.8 dated Aug. 28, 2012, 7 Pages.

* cited by examiner

METHODS FOR DELIVERY OF SCREWS FOR JOINT FUSION

CROSS REFERENCE TO RELATED APPLICATIONS

This application is a continuation of copending U.S. patent application Ser. No. 14/149,197 filed Jan. 7, 2014 to Stark entitled "Methods for Delivery of Screws for Joint Fusion," which is a continuation of U.S. application Ser. No. 12/651,843 to Stark, filed on Jan. 4, 2010, entitled "Bone Screws and Particular Applications to Sacroiliac Joint Fusion," which is a continuation of U.S. application Ser. No. 11/879,536 to Stark, filed on Jul. 17, 2007, entitled "Bone Screws and Particular Applications to Sacroiliac Joint Fusion," all of which are hereby incorporated by reference.

FIELD OF THE INVENTION

The invention relates to methods for fusing the sacroiliac joint using anchors that distract the joint and immobilize the joint in its distracted position. The invention further relates to bone screw designs that are versatile with respect to firm anchoring in softer or harder bone structures through increasing gripping of the structure as the screw is advanced.

BACKGROUND OF THE INVENTION

Lower back pain is a common ailment among the population and results in pain and suffering as well as loss of work time. Thus, approaches for the treatment of back pain can both relieve suffering as well as reduce employee sick time. Since back pain results in considerable employee absenteeism, effective treatments for lower back pain have both economic benefits as well as the benefit of alleviating considerable suffering.

The sacroiliac joint is located at the juncture of the ilium, the upper bone of the pelvis, and the sacrum at the base of the spine. While the sacroiliac joint has a limited range of motion, dysfunction of the joint has been identified. The joint is supported by a range of ligaments including, for example, the sacroiliac ligament at the base of the joint and the anterior sacroiliac ligament at the top of the joint. The joint is in the vicinity of the passage of a large number of blood vessels and nerves that pass from the torso to the lower extremities. Any procedures near the joint should avoid damage to the adjacent vessels and nerves.

SUMMARY OF THE INVENTION

In a first aspect, the invention pertains to a method for fusing the sacroiliac joint in which the method comprises drilling, selecting an implant and inserting the implant. In particular a bore is drilled into the joint between the sacrum bone and iliac bone to prepare the joint for insertion of an implant. A threaded implant is selected based on the prepared joint in which the implant or screw is selected to distract the joint upon insertion and maintains or increases tension upon insertion. The implant can have a varying structure along its length. The selected implant can be inserted into the bore within the sacroiliac joint between the sacrum bone and iliac bone to immobilize the joint. In some embodiments, material is also placed into the joint or as a component of the implant to promote bone growth before, during or following completion of the procedure to deliver an implant.

In further aspects, the invention pertains to a method for fusing the sacroiliac joint using an implant. The method can comprise screwing an implant into the sacroiliac joint between the sacrum bone and the iliac bone in which the implant comprises a shaft, a tool engagement flange at top end of the shaft, a pointed tip comprising no more than about 20 percent of the length of the screw, and threads spiraling around the shaft. In some embodiments, the volume displacement of the threads perpendicular to the shaft increases at least about 5 percent from a point adjacent the tip to a point near the top of the shaft.

In additional aspects, the invention pertains to a medical implantable screw comprising a headless shaft, a tool engagement flange at top end of the shaft, a pointed tip comprising no more than about 20 percent of the length of the screw, and threads spiraling around the shaft. In some embodiments, the volume displacement of the thread increases at least about 5 percent from a point adjacent the tip relative to a point near the top of the shaft and wherein the screw comprises one or more biocompatible materials.

In other aspects, the invention pertains to a method for inducing bone in-growth for joint fusion or bone repair. The method comprises placing a blend of a bone powder alone or in combination with a bioactive agent that induces bone growth into a joint or bone fracture. In some embodiment, the bioactive agent induces bone growth.

Furthermore, the invention pertains to a composition comprising a blend of bone powder and a bioactive agent that simulates bone growth.

In addition, the invention pertains to a method for selecting an orthopedic implant. The method comprises placing a sizing element into a prepared location for a bone screw and tightening the sizing element with a torque wrench to evaluate the size of appropriate bone screw for implantation into the site.

In further aspects, the invention pertains to an orthopedic implant comprising a bone replacement materials and a bone growth stimulating biologically active agent. The bone replacement material is a bio-resorbable polymer, a natural or synthetic bone composition or a combination thereof. The biologically active agent generally is blended into the bone replacement material composition

DETAILED DESCRIPTION OF THE INVENTION

Figure 1:
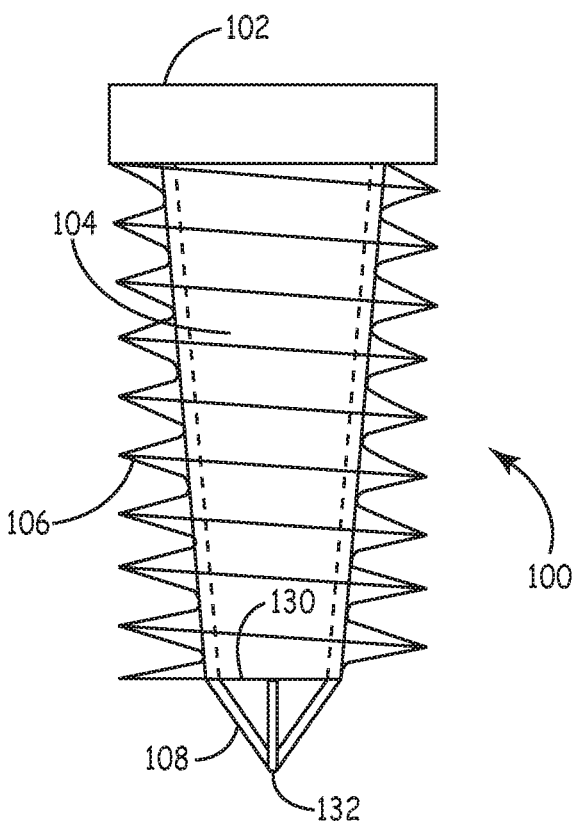
FIG. 1 is a side view of an embodiment of an implant having a head and a pointed tip.

Improved fusion of the sacroiliac joint can be accomplished with implants, e.g., screws that are designed to distract the joint with spreading forces as they are screwed into the joint. In particular, the sacroiliac joint can be successfully fused through the insertion of an implant directly into the gap of the joint between the iliac bone and sacral bone with the implant gripping bone on the respective sides of the joint. If the implant is designed properly to increase distraction of the joint as it is advanced into the joint, the implant can be selected to screw tightly into the joint to stably fuse the joint. The placement of the implant can be prepared through drilling, impacting or the like. An implant can be selected that screws into the resulting bore and tightens with a desired amount of tension. In some embodiments, the threads of the improved screws have threads that increase in volume displacement from the tip to the head to provide greater spreading forces as the screw is inserted.

The sacroiliac joint has some properties that make the joint challenging for fusion. Pioneering work has demonstrated that fusion of the sacroiliac joint using implants and the like placed into the joint between the sacrum bone and iliac bone can alleviate chronic debilitating lower back pain where there is no other identifiable source. While the sacroiliac joint does not move large distances, wear, damage and/or concentration of forces to the joint evidently can result in intense pain. Due to the complexity of the joint, inaccessibility to the joint surfaces and the major nerve and vascular structures passing adjacent the joint, the joint is not presently amenable to joint replacement. Similarly, the joint is not amenable to revision, realignment or reconstruction. The joint is held together by a network of ligaments that hold the joint together to resist distracting forces.

The sacroiliac joint generally can have significantly differing bone characteristics across the joint. At points where the load is carried, the bone can be hard while closely neighboring bone can be relatively soft. Thus, a fusion procedure can encounter significantly different bone on different occasions and even at different locations across the placement of the implant during a single procedure. While the procedures described herein comprise identification of the boundaries of the joint, placement of the implant within the joint generally is selected without information on the character of the underlying bone since the locations of the force load across the joint cannot be easily measured.

In some embodiments, design of improved screws for the immobilization of the sacroiliac joint can provide desirable screw configurations for general bone screws. In particular, the screws can be selected to provide good gripping whether or not the bone encountered is relatively hard or relatively soft. For implantation into the sacroiliac joint, it is desirable for the bone to distract the joint through the direction of spreading forces from the screw. Thus, in some embodiments, the screw can be designed to have characteristics that differ at different positions along the length of the screw. For example, the distraction of the joint can increase as the screw is implanted into the joint. In some embodiments it is desirable to select the shape of the screw, e.g., the core and/or the threads, such that the screw grips more strongly as the screw is advanced. Other portions of the procedure, such as drilling and post-implantation processing of the joint, can also be adapted for the immobilization procedure to take better advantage of the procedure's objectives of distracting and stabilizing the joint.

In general, bone screws can be used to stabilize a crushed bone structure, attached fractured bone elements to each other, attach an object, such as a ligament or tendon, to a bone and/or immobilize a bone joint. A considerable amount of development has been devoted to spinal screws to stabilized crushed or damaged spinal disks. In spinal applications, the purpose of a spine cage can be space filing. However, other applications generally can involve gripping by the screw based on spreading forces extending radially outward from the axis of the screw. A head on the screw may or may not be desired for facilitating transfer of axial forces into spreading forces.

In order for the screw to grip more tightly as the screw advances, it can be desirable for the displacement of the screw to increase as the screw is driven into the bone/joint. This increased displacement can be accomplished through an increase in the core diameter, an increase in the thread displacement or both. The threads may or may not change along the length of the screw. For example, the thread thickness can increase from the screw tip to the screw head, the lateral extent of the threads can increase from the tip to the head and/or the thread spacing can decrease from the tip to the head. Similarly, there may or may not be a second set of threads between a first set of threads. With a screw that provides increasing displacement as the screw is inserted, the screw tightly grips as it is inserted into the sacroiliac joint.

Screws have a general structure with a tip and a top at the opposite end from the tip. The top may or may not include a head. However, the top generally comprises a flange to engage a driving tool. Threads spiral around a core of the implant, although threads can be discontinuous in some embodiments without significantly changing their function. The tip may or may not have cutting flutes. The core may or may not be porous, fenestrated, hollow and/or cannulated. In some embodiments, the character of the screw changes along the length of the screw from the tip to the top. The character may or may not change uniformly or monotonically, but on average the implant can be designed to maintain or increase tension upon insertion.

In some embodiments, the improved implant for the sacroiliac joint is a tapered screw. Tapered screws for sacroiliac immobilization/fusion are also described in the present inventor's copending U.S. patent application Ser. No. 10/797,481, filed on Mar. 10, 2004, now U.S. Pat. No. 7,648,509, entitled "Sacroiliac Joint Immobilization," incorporated herein by reference. In general, the tapered screws can have tapered cores, tapered threads or both. While a taper can increase the displacement of the implant from the tip toward the head, other parameters can similarly increase the thread displacement along the length of the implant. For example, threads can have increased displacement through an increase in thickness that correspondingly increases displacement resulting from increased thread volume.

The improved procedures and tools described herein can be used for either open or closed procedures. In open procedures, the joint is surgically opened to visual observation of the joint. Once the boundaries of the joint are identified, the location for the implant can be drilled out, such as with a powered mechanical reamer or drill. Care should be taken to stay within the joint to avoid contacting any blood vessels or nerves, of which there are significant members that pass close to the sacroiliac joint. The size of the reamer or drill bit can be selected based on the size of the individual or other suitable parameters based on an examination of the patient.

An implant is then selected to distract and fuse the joint. As noted above, implants of particular interest have structures that vary along the length of the implant to maintain or increase tension as the implant is inserted into the bore that is formed by the drilling. The implant is screwed into the joint to provide the desired amount of distraction forces at its full placement. The selection of the screw can comprise the use of a sizing element, which can be used with a wrench, such as a torque wrench, to select a correctly sized and characterized implant to screw into the joint within a desired range of torque parameters.

In some embodiments, a sizing system can comprise a set of exchangeable sizing elements that have an outer shape approximating the outer shape of the implants. The set of sizing elements can include, for example, an element corresponding to each size of available implants. The sizing elements can be made from a material that can be easily sterilized, such as stainless steel or other metal, so that the sizing elements can be sterilized and reused. In some embodiments, a torque wrench can provide a display output of the applied torque for monitoring by the health care professional or the wrench can be a torque limiting wrench that limits the amount of torque that can be applied so that the applied torque does not exceed an upper limit. Suitable torque limits for implant placement can be in some embodiments from about 0.5 Newton-meters to about 12 Newton-meters and in other embodiments form about 0.75 Newton-meters to about 8 Newton-meters. Torque limiting wrenches are described further in U.S. Pat. No. 6,162,053 to Hollander, entitled "Analog Dental Wrench," and U.S. Pat. No. 6,807,885 to Loper, entitled "Torque Limiting Wrench for an Ultrasonic Medical Device," both of which are incorporated herein by reference.

The sizing elements can be inserted into the prepared joint at a desired amount of torque. If the sizing element holds at the selected torque, the correspondingly sized implant can be used following removal of the sizing element. In this way, the health professional can avoid the accidental selection of an implant that is too small. If an implant is selected that is too small, the implant may strip out when it is being implanted, which would then require the subsequent use of a larger implant. Since the implants generally cannot be reused, the initially selected implant that was too small can be wasted. Thus, the use of the sizing system can result in the waste of fewer implants since the correct size implant can be selected more accurately.

After completing the insertion of the implant, bone materials can be placed into the joint to promote bone in growth that further supports immobilization. In particular, crushed bone material, demineralized bone matter, synthetic bone material or compositions or corresponding putties can be placed into the joint. Additionally or alternatively, bone morphogenic protein or other similar bone growth stimulating compositions can be placed into the joint to stimulate bone growth to immobilize the joint. In particular, it can be desirable to blend powdered, natural or synthetic bone material with a bone growth composition, such as bone morphogenic protein, for placement into the joint or other bone fracture to stimulate bone growth with the bone material as a foundation.

In the closed or less invasive procedures, a cannula can be placed into the joint as guided by a pin or the like. The position of a pin to guide the implant can be placed once other pins have been used to identify the boundaries of the joint. Various imaging approaches can be used to guide the process of finding the boundaries of the joint without opening the joint up for visual inspection. The cannula exposes a small opening to the joint at the selected location of the implant placement. The cannula can then guide the drilling and/or implant insertion steps in a procedure that is less disruptive to the patient.

In general, approaches to the sacroiliac joint lack easily dissectible tissue planes that provide dissection between muscles or between nerves. Large adjacent nerves, such as the sciatic nerves, and arteries, such as the iliac vessels, limit the approach to the joint and preclude certain access. The nearby vessels and nerves also greatly magnify the risk of error. Similarly, the close location of the spine also provides limits to access as well as further contributing to the risks.

The sacroiliac joint bone anatomy has a structure specifically for the non-intuitive passage of force through the joint with the weight of the torso transmitted to the hips. This transfer of forces generally takes place whether seated or standing. The bone mass associated with the sacroiliac joint is limited and is not amenable to build up or reconstitution. Thus, procedures are generally designed to avoid sacrificing unnecessary amounts of bone support. In particular, drilling or impacting a bore within the joint should provide appropriate gripping of the implant without excessively weakening of the surrounding bone.

The bones around the joint exhibit complex coupled motions of angulation, rotation and squirm. There is often little or no significant sliding or translation of surfaces over each other. Articular cartilage on one surface rests against fibrocartilage on the other surface, which is unique in the body. In contrast, there are closely coupled combinations with small degrees of relative motion of generally less than one degree in rotation or one millimeter in translation. Periarticular ligamentous structure combined with distant encompassing structure controls the joint. At the same time, most muscles cross the joint in a complex way. Most muscles cross several joints and/or disk spaces and transfer forces and balance forces between the plurality of joints at the same time. Also, many muscles that technically do not cross the joint help to control the joint.

Pain can result from the joint due to one or more pathologies. Congenital defects, such as smallness or malformation, can result in pain. Acquired laxity of the joint can result from pregnancy or due to congenital conditions. Trauma, such as falls, can result from direct incongruities that are secondary to pelvic or sacral fractures or from ligamentous disruption. Furthermore, inflammatory syndromes, such as septic arthritis or rheumatic conditions can similarly result in pain in the sacroiliac joint. Also, age results in an increasingly irregular topography of each side of the joint with progressive changes in the surface topography distributing unusual forces across the joint. Following performance of the procedure, the fused joint is fixed in a manner suitable to resist weight bearing stresses.

The procedures described herein are selected to improve the uniformity of results from sacroiliac fusion procedures. Similarly, the procedures generally can be used with more consistent results by a medical professional with less training and experience than procedures using less well designed procedures. The implants are more specifically designed for use in the sacroiliac joint or for other orthopedic applications that encounter bone structures of varying type during the procedure. These implants yield more reproducible results relative to other implants, such as spinal implants, that are designed for other types of application, which can be inserted into the sacroiliac joint in a fusion procedure.

As noted above, the procedures and implants described here can be used advantageously for other orthopedic applications in which different types of bone structures can be encountered, such as a hard outer bone and a soft inner bone. For example, the implants can be used for the reattachment of severed ligaments where the implant is directed into a bone structure to perform the reattachment. In these applications, it can be desirable to have an implant with changing structure along the length of the implant.

Screw Structures and Materials

Screws of particular interest have changing parameters from the tip to the head. These changing parameters can be selected to result in the maintenance or increase of tension upon insertion into properly prepared boned or joints. In some embodiments, the screws are tapered. Various thread designs are appropriate to form desired screws that have desired retention while providing desired amounts of dissection with spreading forces, which are desirable for insertion into, for example, a sacroiliac joint.

Figure 2:
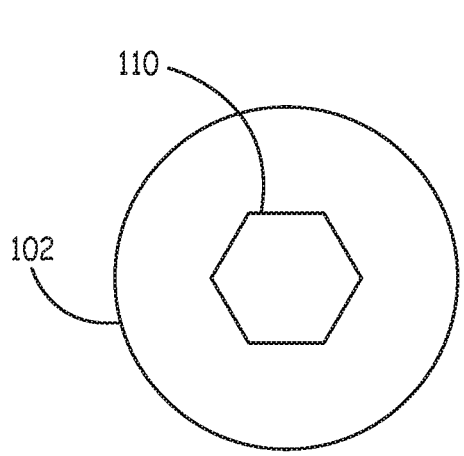
FIG. 2 is a top view of the implant of FIG. 1.

Referring to FIG. 1, an embodiment of an orthopedic screw 100 is shown schematically. Screw 100 comprises head 102, core 104, threads 106 and tip 108. Head 102 is optional. Head 102 has its conventional meaning as a terminal element having a lateral extent larger than the core adjacent the head. Generally, head 102 comprises a driving tool engagement flange 110, as shown in FIG. 2. Tool engagement flange 110 can have any reasonable shape to engage a driving tool, such as a straight channel, a cross channel, a hexagonal depression or appropriate extensions. As described further below, a tool engagement flange can be located along the top surface of the core for embodiments lacking a head. In some embodiments, the tool engagement flange can extend significantly into the core of the screw to provide an extended interface for engaging a drive tool.

Figure 3:
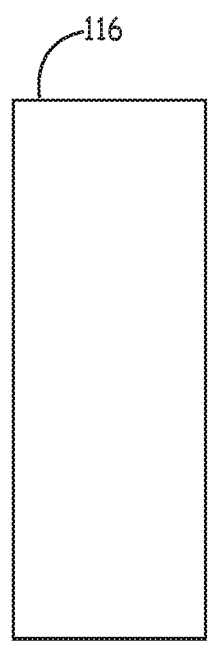
FIG. 3 is a side view of an implant core having an approximately constant core diameter over the length of the implant.

Core 104 connects head 102 with tip 108 and supports threads 106. The core is the portion of the body of the screw without the threads. As shown in FIG. 1, core 104 is tapered. An embodiment of a constant diameter core 116 is shown in FIG. 3. Core 104 can be tapered independent of the overall screw. In particular, if the core is generally cylindrical, the threads can have changing lateral extent along the length of the screw to result in a tapered screw. Similarly, if the core is tapered, the lateral extent of the threads can be constant to lead to the same taper for the screw, the lateral extent of the threads can change along the length of the screw to contribute further to the taper of the screw or the threads can change along the length of the screw to decrease or eliminate the overall taper of the screw, as shown, for example, in FIG. 1.

Figure 5:
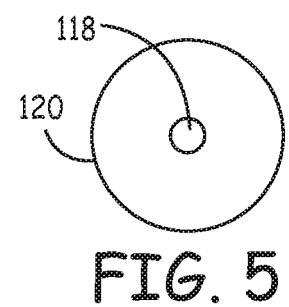
FIG. 5 is a top view of the core of FIG. 4.
Figure 4:
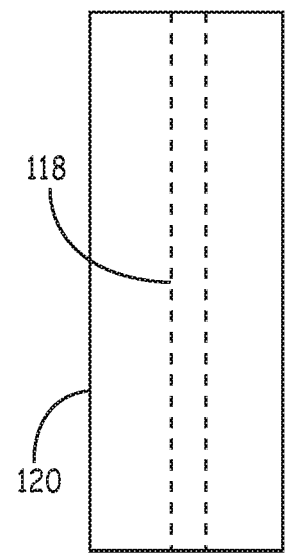
FIG. 4 is a side view of a cannulated implant core having an approximately constant core diameter in which the path of the core channel is outlined with phantom lines.
Figure 6:
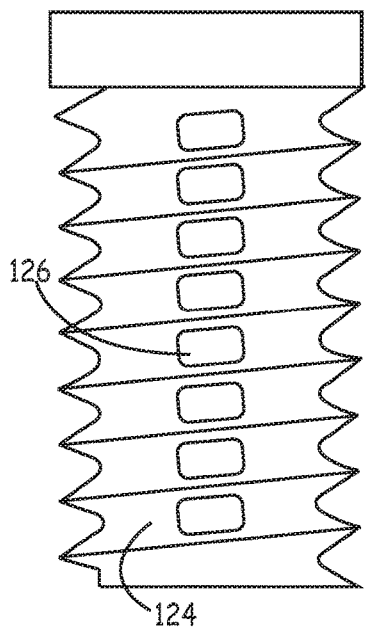
FIG. 6 is a side view of a hollow, fenestrated implant.

Core 104 can be, for example, solid, hollow or cannulated. In the cannulated embodiments, a channel 118 ends through the entire length of core 120 such that the screw can be delivered over a pin or the like, as shown in FIGS. 4 and 5. Channel 118 would similarly extend through a head or tip if present. Hollow cores can also be fenestrated to provide for bone in growth into the hollow core. For example, referring to FIG. 6, core 124 has openings 126 into the hollow interior of core 124. The top of a hollow core screw can be reversibly openable, such as being threaded, such that bone material or other similar materials, can be inserted to promote bone in growth. Fenestrated spinal fusion cages that can be filed with bone material is described, for example, in U.S. Pat. No. 4,961,740 to Ray et al., entitled "V-Thread Fusion Cage and Method of Fusing a Bone Joint," and U.S. Pat. No. 5,669,909 to Zdeblick et al., entitled "Interbody Fusion Device and Method for Restoration of Normal Spinal Anatomy," both of which are incorporated herein by reference.

In general, threads 106 can have a variety of characteristics. In some embodiments, the threads have changing characteristics along the length of the implant. As shown in FIG. 1, threads 106 have a smaller lateral extent from the tip to the head, such that the edge of the threads form a generally cylindrical outer surface of the screw even though core 104 has a diameter that increases toward the head. Some of the thread characteristics of particular interest are described in detail below with respect to some specific embodiments.

Referring to FIG. 1, tip 108 generally can be identified by an abrupt change in structure at a boundary 130. Tip 108 can have a point 132. Also, tip 108 can comprise cutting flutes 134 or the like to facilitate insertion of the screw. If it is ambiguous whether or not a particular implant has a separate tip, the 15 percent of the length of the implant away from the head/top can be considered the tip adjacent the threaded core. Tip 108 may or may not be threaded.

For implantation into a sacroiliac joint between the sacrum bone and iliac bone, it can be desirable to use an implant that is headless such that there is no head sticking up from the joint after the procedure that can cause irritation to the patient. However, headless screws do not transfer axial forces to spreading forces when the top of the screw reaches the surface of bone. Thus, the screw should be designed to provide spreading forces to distract the joint without the need for a head to contact the bone surface.

Figure 7:
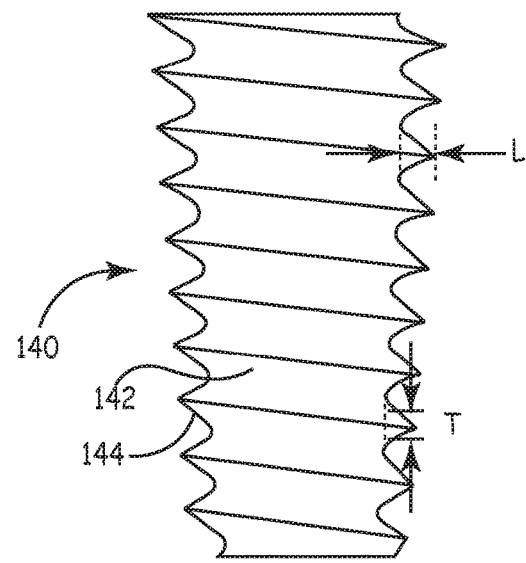
FIG. 7 is a side view of a headless implant with a tapered core.

An embodiment of a headless screw is shown in FIG. 7. Screw 140 comprises core 142, threads 144 and drive flange 146, shown in FIG. 8. Drive flange 146 is located along top surface 148 at the top of core 142. In this embodiment, core 142 is tapered such that the core has a smaller diameter near the tip of the screw and a larger diameter near the top of the screw adjacent the drive flange. Threads 144 spiral around core 142 and have a roughly symmetrical shape relative to the top surface of the thread and the bottom surface of the thread. Also, threads 144 have a roughly constant lateral extent from the core. The lateral extent "L", as shown in FIG. 7, is the distance from the core to the edge of the thread. Thus, the diameter of the threads in screw 140 increases from the tip to the head of the screw due to the taper of the core and not due to a change in the lateral extent of the threads. In alternative embodiments, the core can be tapered over a portion of the length of the screw with a constant or counter tapered shape over other portions of the screw while providing desired degrees of joint distraction.

Figure 8:
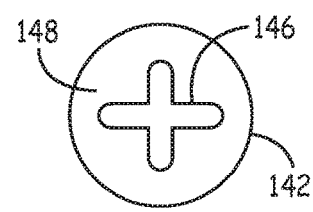
FIG. 8 is a top view of the implant of FIG. 7.
Figure 9:
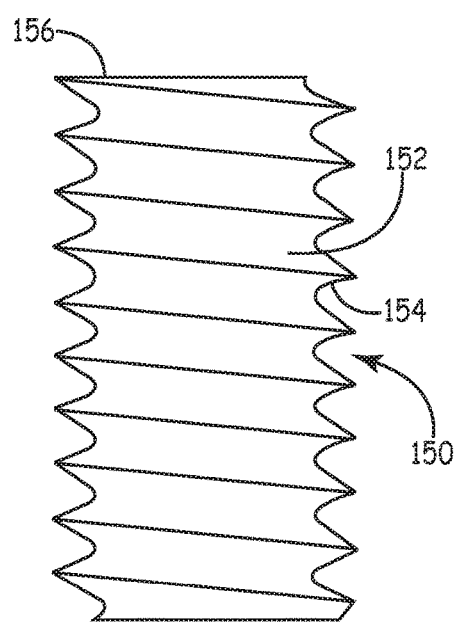
FIG. 9 is a side view of an implant with a generally cylindrical core and tapered threads.

Another embodiment of a tapered bone screw is shown in FIG. 9. In this embodiment, screw 150 comprises a core 152 and threads 154. The top 156 of core 152 has a drive flange, which can be, for example, the same as shown in FIG. 8. In this embodiment, core 152 has an approximately constant diameter along the length of the screw extending along the axis of the screw. However, the lateral extent of the threads increases from the tip to the top of the screw. Thus, the diameter of the threads and the overall screw diameter correspondingly increase as a result of the increased thread lateral extent even though the core has a constant diameter. Threads 154 have an asymmetric shape with a flatter top surface relative to a more angled lower surface. Asymmetric threads are discussed in more detail below. In alternative embodiments, the core is tapered and the lateral extent of the threads changes such that there are two contributions to the overall taper of the screw.

Figure 10:
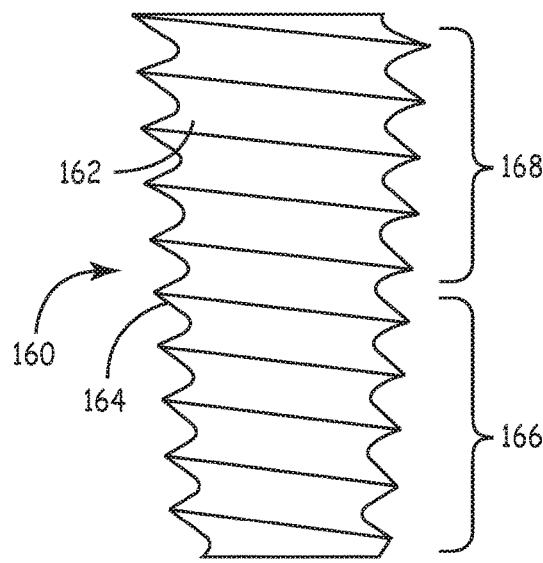
FIG. 10 is side view of a tapered implant with a changing thread pitch.

Another embodiment of a tapered bone screw is shown in FIG. 10. Screw 160 is also a headless screw comprising a core 162 and threads 164. Top surface 166 of core 162 has a driver flange, which can be, for example, the same as shown in FIG. 8. Core 162 has a taper in this embodiment, although in other embodiments the core can have a constant diameter. In this embodiment, threads 164 have two segments 166, 168 with different pitch. In particular, threads 168 have adjacent threads closer to each other than threads 166. In this embodiment, the thread pitch change is relatively abrupt, although in other embodiments the thread pitch can change gradually. Similarly, the other embodiments, the threads can have three or more sections with different pitch from each other.

Figure 11:
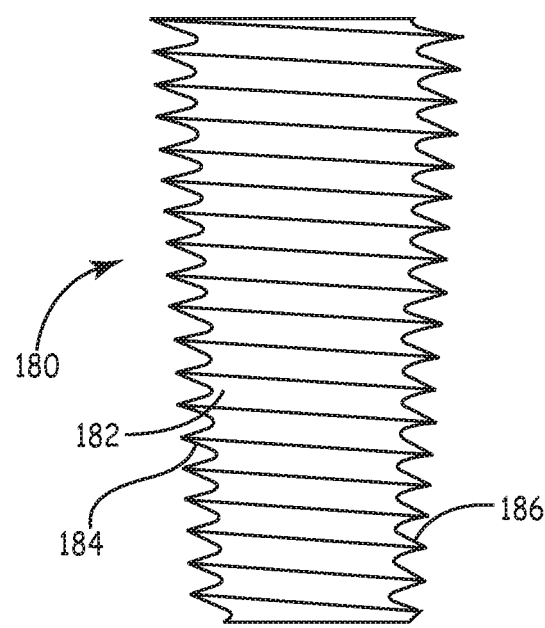
FIG. 11 is a side view of a tapered implant with two sets of co-axial threads.

An embodiment of a tapered bone screw 180 is shown in FIG. 11 in which the screw has two sets of interwoven, coaxial threads. Specifically, screw 180 comprises a core 182, first threads 184 and second threads 186. Second threads 186 spiral around the core between the threads of first threads 184. The properties of the two sets of threads can be selected as desired. In general, two sets of threads can be combined with other screw features described herein, such as headed or headless screws, tapered cores or cylindrical cores, etc.

In general, for appropriate embodiments the screws should have appropriate dimensions for insertion into the sacroiliac joint between the sacrum bone and iliac bone. The screw should provide desired immobilization of the joint without damaging the surrounding bone. For embodiments with a screw head the head can have any reasonable dimension based on the overall screw dimensions.

For insertion into the sacroiliac joint, the length should be selected such that the implanted screw, except possibly for an optional screw head should be contained with in the joint. For a typical adult human, the screws then can have a length from about 10 millimeters (mm) to about 45 mm, and in other embodiments from about 15 mm to about 35 mm. For other orthopedic applications, suitable lengths of the screw generally range from about 10 mm to about 80 mm. A person of ordinary skill in the art will recognize that other ranges of screw lengths within the explicit ranges above are contemplated and are within the scope of the present disclosure.

Similarly, for insertions within a sacroiliac joint, the screw should have a diameter that is consistent with distracting the bone without being too large such that the bone is damaged through its insertion. For a typical adult human, appropriate screw would have an average diameter from about 6 mm to about 28 mm, and in other embodiments from about 8 mm to about 25 mm. A person of ordinary skill in the art will recognize that additional ranges of diameters within the explicit ranges above are contemplated and are within the scope of the present disclosure. If the screw is tapered, the leading diameter and trailing diameter correspond with the amount of taper and the average diameter.

In general, the screw taper can be determined as the angle of the screw edge relative to the screw axis. In general, the taper can be at least about 1 degree, in further embodiments at least about 2 degrees, in other embodiments from about 3 degrees to about 12 degrees, and in additional embodiments from about 3.5 degrees to about 10 degrees. As noted above, the taper can result from a core taper, a variation in the threads of the lateral extent or both. The range of core tapers can generally range over the same ranges of angles given above for the overall taper of the screw. Of course, a taper does not need to be linear, so that the surface of the screw can be curved. For curved tapers, the angle can be estimated from threads adjacent the tip and the top to provide a reasonable estimate of the angle of the overall taper.

In general, the threads can have several parameters to characterize the nature of the threads. For example, the thickness of the thread can be evaluated at the point half way from the edge of the thread to the core. This thickness "T" is noted in FIG. 7 for reference. The thickness can be related to the sharpness of the thread. The edge of the thread can be sharp, but generally it is desirable for the edge of the thread to be rounded. As shown in FIG. 7, the threads meet the core along smooth curves. Smooth transitions at the edges of the elements avoid the undesirable concentration of forces along the bone that can result in a poor interface between the bone and screw. The cross sectional shape of the threads can be approximately symmetrical or in other embodiments asymmetrical relative to the top and the bottom of the threads.

The top of the thread is oriented toward the top of the screw while the bottom of the thread is oriented toward the tip of the screw. The leading and trailing edges generally have different functions so that it may be desirable for these surfaces to have different shapes from each other. For example, the top thread surface may push outward on the bone while the lower surface may cup or compress the bone longitudinally as it pulls the screw deeper.

The thread dimensions can be selected to achieve the desired distraction and gripping properties of the screw upon implantation. The average lateral extent of the screw can be 0.25 to 2.5 millimeters and in other embodiments from about 0.4 to about 2.0 millimeters. In some embodiments, the lateral extent of the thread tapers along the length of the screw with a greater lateral extent of the thread near toward the top of the screw, such as shown in FIG. 9. For these embodiments, the lateral extent of the tapered threads can be at least about 0.1 mm and in further embodiments at least about 0.25 for the smaller threads, and the larger lateral extent of the threads of the screw can be no more than about 3.5 mm and in further embodiments no more than about 3 mm. In some embodiments, the variation in the lateral extent of the threads is monotonic along the length of the screw optionally excluding the last turn of the threads at the top and/or at the tip.

The average pitch of the threads can be generally from about 1 mm per turn to about 4 mm per turn, and in further embodiments from about 1.5 mm per turn to about 3.5 mm per turn. As noted above, the pitch of the threads can be constant over the length of the screw or the pitch of the threads can change over the length of the screw or a portion thereof. In general, it is desirable for the threads to have smooth surfaces at the edge of the threads as well as at the meeting of the threads with the core. Thus, while the threads can be sharp, smooth surfaces of the threads can avoid discontinuities that can result in undesirable concentration of forces. However, in some embodiments, discontinuous thread surfaces can result in a desirable concentration of forces.

In general, the implants/screws can be formed from any suitable biocompatible material, which is non-toxic. The material can be biologically effectively inert or can impart specific desired biological effects, such as through the elution of bone morphogenic protein. Suitable biocompatible materials can include, for example, metals, such as stainless steel, tantalum and titanium, rigid polymers, such as polycarbonates and polyetheretherketone (PEEK), ceramics, such as alumina, or composites, such as carbon composites or carbon fiber composites. In some embodiments, the screws can comprise a bioresorbable polymer, such as poly(hydroxyacids), poly(epsilon-caprolactone), polylactic acid, polyglycolic acid, poly(dimethyl glycolic acid), copolymers thereof and mixtures thereof. The screws can be formed, for example, using conventional machining, molding or the like. The screw or its surface can be porous. For example, porous tantalum is commercially available for forming the screw. In addition, synthetic bone materials and/or sterile bone materials, either allograft or xenograft materials, can be used to form the implantation elements. Suitable synthetic bone material includes, for example, coral and calcium compositions, such as hydroxyapatite, calcium phosphate and calcium sulfate.

In some embodiments, the implant can be formed from a bio-resorbable polymer a natural or synthetic bone material or a combination thereof and a bioactive agent that stimulates bone development, such as BMP. The BMP can be blended with the material prior to molding, casting or otherwise formed into the implant or portion thereof. Generally, if a portion of the implant is formed from the BMP blended with bioresorbably polymer or bone material, this portion can be a support portion, i.e., a portion that provides mechanical integrity to the implant. In appropriate embodiments, as the resorbable polymer biodegrades, bone replaces the implant material. Similarly, for implants formed from the bone material, the implant becomes incorporated into the new bone that forms as a result of the bioactive agent.

Optionally, a bioactive agent can be coated on the surface of the immobilization element. To coat the immobilization device with the bioactive agent, the device can be dipped in a composition comprising the bioactive agent, sprayed with a composition comprising the bioactive agent, painted with the bioactive agent, and/or coated with other processes, such as those generally known in the art. If the coating composition comprises a solvent, the solvent can be allowed to evaporate after applying the coating composition. The bioactive agent can be applied alone as a coating composition or with another agent to control the elution of the agent. The agent can be applied from a solution with a solvent that can evaporate following the application of the coating solution. Also, the bioactive agent can be combined with a control release agent, such as a biodegradable polymer that gradually releases the bioactive agent as the polymer degrades within the patient. Biocompatible, biodegradable polymers are known in the art, such as polylactic acid, poly(glycolic acid) and copolymers and mixtures thereof. A binder may or may not be included to control the elution from the coating. Furthermore, the bioactive agent can be injected or otherwise delivered in the vicinity of the immobilization device. The bioactive agent can be combined with a suitable biocompatible carrier, such as commercially available buffered saline or glycerol.

Suitable biologically active agents include, for example, bone morphogenic protein (BMP) and cytokines. BMP mediates the formation and healing of bone, cartilage, tendon and other bone related tissues. One human BMP polypeptide is described in detail in Published U.S. Patent Application Serial Number 2003/0032098 to Young et al., entitled "Bone Morphogenic Protein," incorporated herein by reference. Suitable cytokines include, for example, human chemokine alpha 2, which is effective to stimulate bone marrow growth. A human cytokine, human chemokine alpha 2, is described in U.S. Pat. No. 6,479,633 to Ni et al., entitled "Chemokine Alpha 2," incorporated herein by reference.

Sacroiliac Joint Fusion Procedure with Distracting Screws

The sacroiliac joint can be successfully fused using a distracting implant that is inserted into the joint between the sacrum bone and the iliac bone with a screw design that maintains or increases tension as the screw is tightened. In general, the joint is prepared by selecting the location of the implant within the joint and exposing the area either through an open procedure or through a cannula for a less invasive procedure. The location selected for the implant can be drilled to prepare the joint for the implant. Following implantation of the screw, filler material can be placed within the joint to further stabilize the joint and promote bone in growth. Additionally or alternatively, bioactive compositions can be used to stimulate bone in growth.

The appropriate approach to the sacroiliac joint for the insertion of an implant is from the patient's back, at or just above the buttocks and slightly displaced form the patient's center line running along their spine. The approach is angled outward back to front. The two openings into the joint are displaced with one accessible from the left and the other from the right. Generally, the health care professional selects one side or the other for immobilization based on an examination of the patient, although in some embodiments, at least one implant is placed on each side of the patient.

The selected side of the joint can be accessed with an open procedure or through a less invasive procedure. In the open procedure, a significant incision is made to expose the joint, and the exposed area is cleared out for desired exposure to the joint. In contrast, for the less invasive procedure, a cannula can be used to form an opening to the joint. Pins can be used to locate the limits of the joint as well as a location for the implant placement. Visualization techniques, such as x-ray visualization, can be used to facilitate pin placement. Drilling and implant placement can be performed through the cannula. Closed procedures for immobilization of the sacroiliac joint through placement of an implant into the joint is described further in Applicant's copending U.S. patent application Ser. No. 10/797,481 filed on Mar. 10, 2004, now U.S. Pat. No. 7,648,509, entitled "Sacroiliac Joint Immobilization," incorporated herein by reference.

Figure 12:
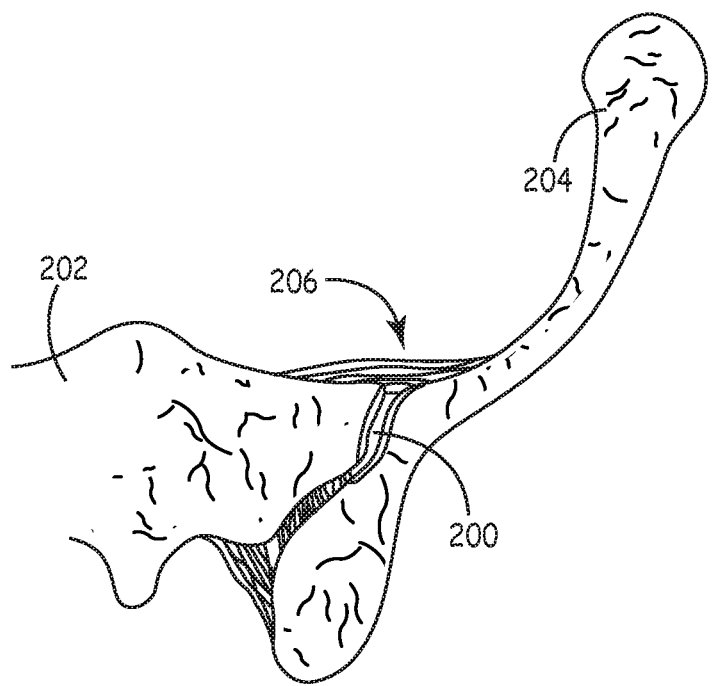
FIG. 12 is a sectional view of the sacroiliac joint.
Figure 13:
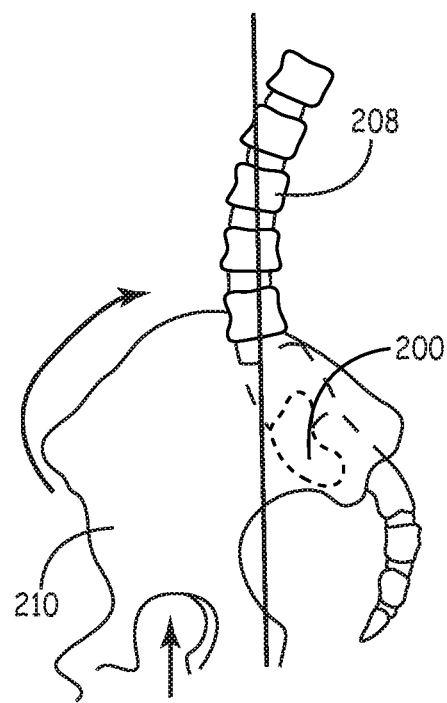
FIG. 13 is a side view of the sacroiliac joint with hidden vertebrae and the sacroiliac joint shown in phantom lines.

Referring to FIG. 12, portion of the sacroiliac joint is shown. As noted above, the sacroiliac joint 200 is located between the sacrum 202 at the base of the spine and the ilium 204, the upper bone of the pelvis. As shown in FIG. 12, various ligaments 206 support the joint. Referring to FIG. 13, walking and other movement apply torque on the sacroiliac joint 200. As shown in FIG. 13, sacroiliac joint 200 is shown with phantom lines between the spine 208 and the pelvis 110. This torque on the sacroiliac joint can result in pain if there is injury or disease.

Figure 14:
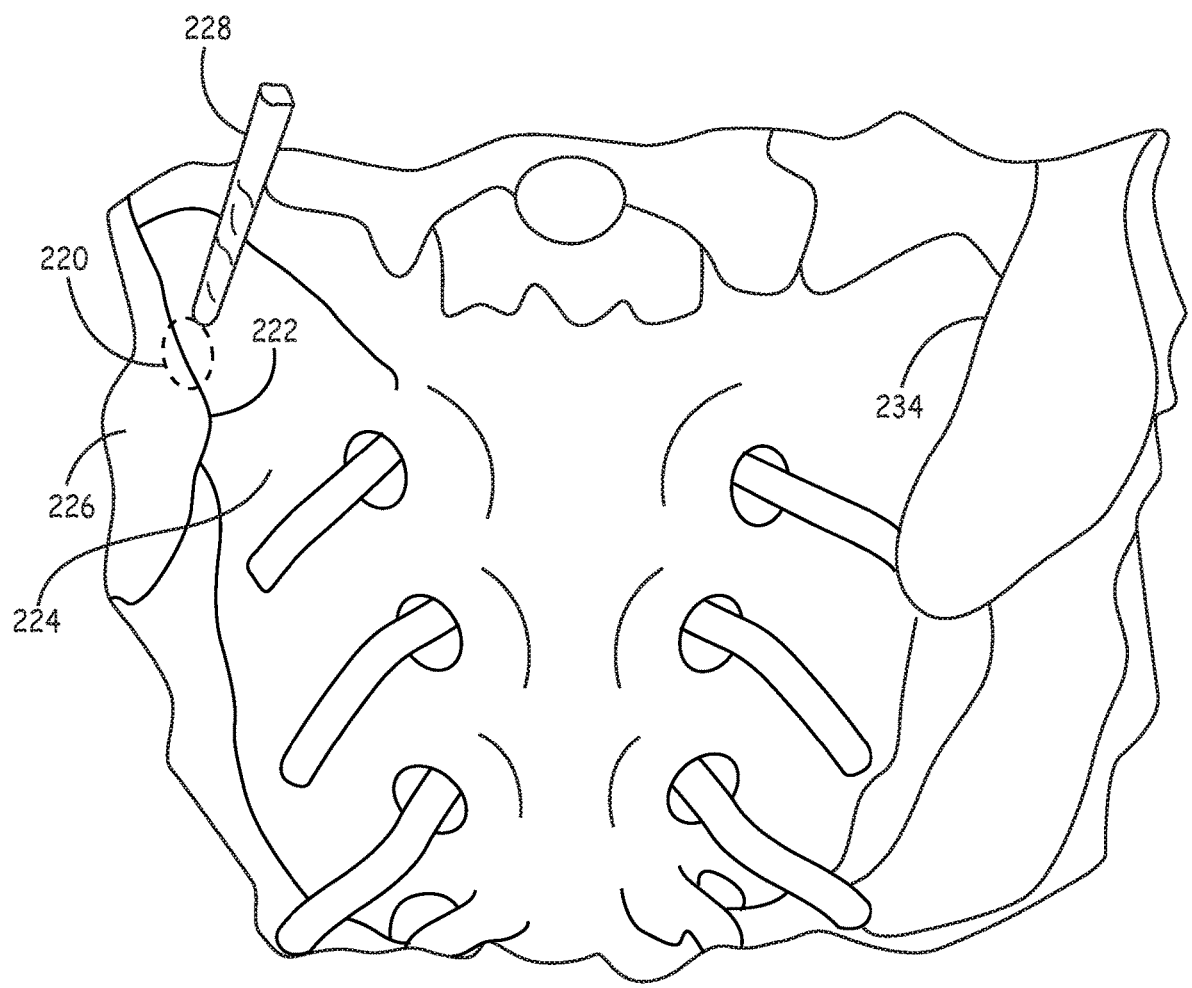
FIG. 14 is a front view of a model of the sacroiliac joint exposed from the tissue with a drill bit positioned to drill a bore into the joint between the sacrum bone and the iliac bone.

Once the selected section of the joint is exposed with an open or a less invasive approach, the site can be prepared using a drill or reamer or impactor. Commercial orthopedic drills are available with a selectable range of drill bits. A powered impactor that can be adapted for the insertion of a sizing element is discussed in U.S. Pat. No. 7,001,393 to Schwenke et al., entitled "Servo-Controlled Impacting Device For Orthopedic Implants," incorporated herein by reference. In addition, impaction of the joint can be performed using a manual or power drill operated with the drill bit rotating backwards so that bone is not removed, but the joint is distracted through impaction by the rotating drill bit in preparation for the placement of an implant. Referring to FIG. 14, a site 220 is identified within the sacroiliac joint 222 between the sacrum bone 224 and the iliac bone 226. A drill bit 228 is shown in FIG. 14 positioned above the drill site 220. During the drilling process, care should be taken not to drill past the joint to avoid injuring any blood vessels or ligaments. The hole can be drilled to have a smaller dimension than the average dimension of the screw so that the screw firmly anchors in place. If the screw has a pointed tip, the drilled bore can have a diameter approximately equal to the smaller diameter of threads along a tapered core.

Figure 15:
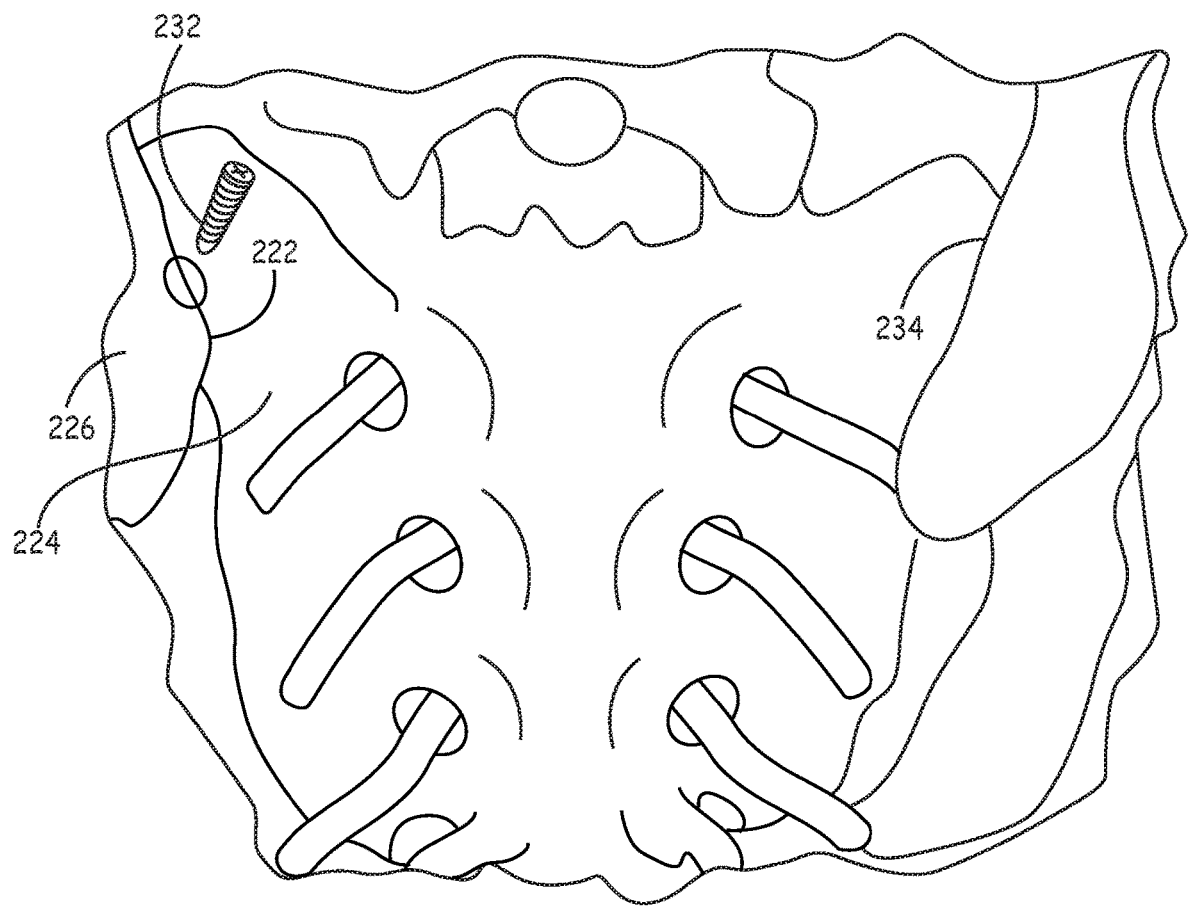
FIG. 15 is a front view of a model of the sacroiliac joint exposed from the tissue with a screw positioned for placement into a bore drilled into the joint between the sacrum bone and the iliac bone.
Figure 16:
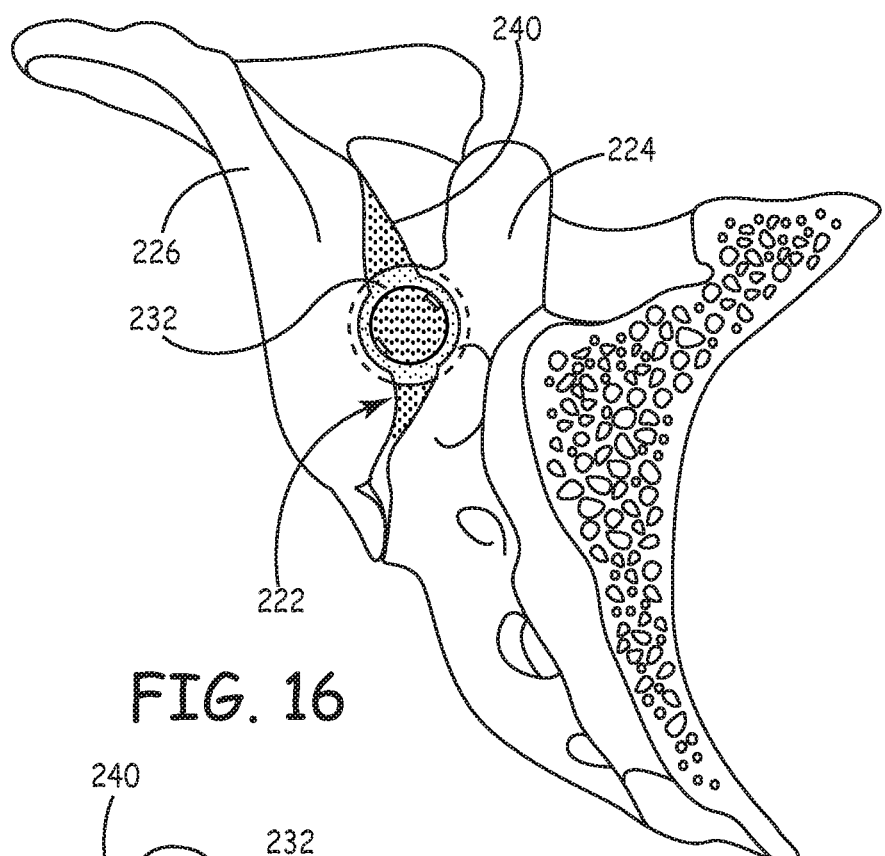
FIG. 16 is a side view depicting the sacroiliac joint with the implant and filler material inserted into the joint between the sacrum bone and iliac bone.
Figure 17:
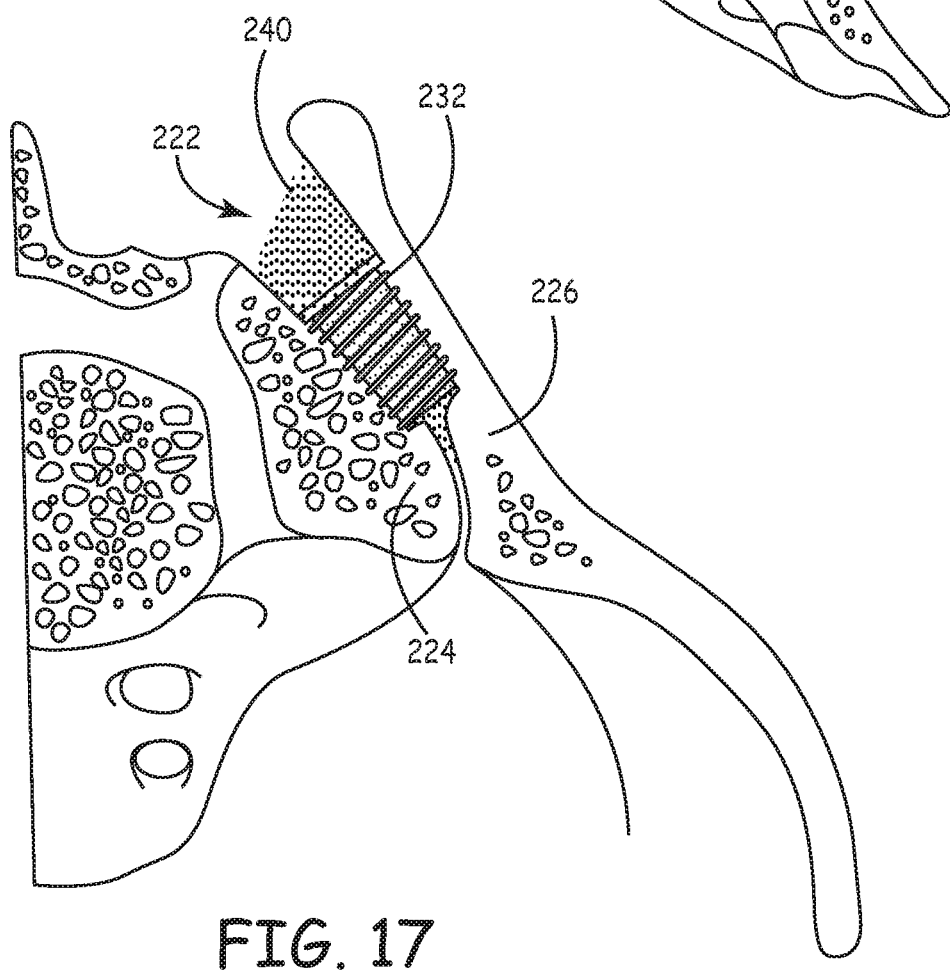
FIG. 17 is a sectional view through the sacroiliac joint showing the implant placed into the joint.

Referring to FIG. 15, once bore 230 is drilled into the joint area between sacrum bone 224 and ilium bone 226, a screw 232 can be screwed into bore 230. As described herein, in some embodiments, screw 232 can be selected to distract the joint during placement. The distraction involves the slight movement away of sacrum bone 224 from ilium bone 226 while stabilizing the joint. As shown FIGS. 14 and 15, an implant is inserted into the left sacroiliac joint. In other embodiments, an implant is inserted into right sacroiliac joint 234, or separate implants are placed into both the left and right sacroiliac joints. The sacroiliac joint with the representative implant is shown in FIGS. 16 and 17 along with additional stabilizing material 240.

Once the screw/implant is inserted into the joint, additional stabilizing material can be placed into the joint. This stabilizing material can be selected to promote bone growth into the joint to further contribute to bone immobilization. Suitable materials include, for example, synthetic bone materials and/or sterile bone materials, either allograft or xenograft materials. Suitable synthetic bone material includes, for example, coral and calcium compositions, such as hydroxyapatite, calcium phosphate and calcium sulfate. The bone material can be placed into the joint as a powder. Suitable material includes, for example, demineralized bone powder, which is commercially available. Gels and putty of demineralized bone powder suspended in glycerol are also commercially available.

Suitable biologically active agents include, for example, bone morphogenic protein (BMP) and suitable cytokines. BMP is involved in formation and healing of bone related tissue, including bone, cartilage and tendon. Suitable cytokines include, for example, human chemokine alpha 2, which is effective to stimulate bone marrow growth. Furthermore, the bioactive agent can be injected or otherwise delivered in the vicinity of the immobilization device.

The biologically active agents can be coated onto an implant for delivery. In some embodiments, it has been found that desirable results are obtained through a blend of biologically active agent, such as BMP, and bone powder, such as demineralized bone powder or crushed bone material, although synthetic materials can be used similarly. The material can be blended and then deposited into the joint, or the materials can be layered into the joint.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention. The incorporations by reference above are intended to incorporate the full disclosures of the references to the extent that the incorporated subject matter is not inconsistent with the explicit disclosure herein, which will not be altered by any incorporation by reference, as well as to incorporate the disclosures with respect to the specific issues referenced in the incorporation.

What is claimed is:

1. A method of stabilizing a sacroiliac joint with an implant, the sacroiliac joint being formed by an opposing sacrum bone and iliac bone, the method comprising:
drilling a bore between the opposing bones of the sacroiliac joint; and
driving the implant into the bore between the opposing bones to distract the joint without piercing entirely through the bones of the joint;
wherein the implant comprises metal, a tapered shaft comprising a core and a thread extending along the core, which is hollow;
wherein the shaft comprises a fenestration opening through a side into the core; and
wherein the drilling and driving steps are performed through a cannula and over a pin.

2. The method of claim 1 wherein at least a portion of the thread is asymmetrical with respect to a shape of a top surface and a bottom surface.

3. The method of claim 1 wherein positioning of the pin is facilitated with imaging.

4. The method of claim 1 further comprising evaluating the joint using a sizing element.

5. The method of claim 4 further comprising selecting a size of the implant based on evaluation of the joint with the sizing element.

6. The method of claim 1 wherein an edge of the thread is sharp along a length of the thread from a head to a tip.

7. The method of claim 1 wherein the implant comprises a head at a first end of the shaft and the core extends from the head, the head having a lateral extent no smaller than the core adjacent the head and a top surface of the head comprises a driver engagement element to engage a driving tool.

8. The method of claim 1 wherein the implant shaft has a porous surface.

9. The method of claim 1 wherein bone material is placed within the fenestration opening prior to the driving of the implant into the joint.

10. A method of stabilizing a sacroiliac joint with an implant, the sacroiliac joint being formed by an opposing sacrum bone and iliac bone, the method comprising:
drilling a bore between the opposing bones of the sacroiliac joint wherein the drilling step is performed over a pin; and
driving an implant into the bore between the opposing bones to distract the joint without piercing entirely through the bones of the joint;
wherein the implant comprises metal, a tapered shaft that comprises a core and a thread extending along the core, wherein at least a portion of the thread is asymmetrical with respect to a shape of a top surface and a bottom surface; and
wherein the implant along the shaft is solid and unfenestrated with a porous surface.

11. The method of claim 10 wherein the drilling and driving steps are performed through a cannula.

12. The method of claim 11 wherein the driving step is performed over a pin.

13. The method of claim 11 wherein positioning of the pin is facilitated with imaging.

14. The method of claim 11 further comprising evaluating the joint using a sizing element.

15. The method of claim 14 further comprising selecting a size of the implant based on evaluation of the joint with the sizing element.

16. The method of claim 10 wherein an edge of the thread is sharp along a length of the thread from a head to a tip.

17. The method of claim 10 wherein a head at a first end of the shaft is a terminal element having a lateral extent larger than the core adjacent the head and a top surface of the head comprises a driver engagement element to engage a driving tool.

18. The method of claim 10 wherein a top surface of the thread is flatter relative to a curved lower surface of the thread.

19. The method of claim 10 wherein the core has a tip comprising a cutting flute.

* * * * *